United States Patent
Kertesz et al.

(10) Patent No.: US 10,060,838 B2
(45) Date of Patent: Aug. 28, 2018

(54) CAPTURE PROBE

(71) Applicant: UT-Battelle, LLC, Oak Ridge, TN (US)

(72) Inventors: Vilmos Kertesz, Oak Ridge, TN (US); Gary J Van Berkel, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 616 days.

(21) Appl. No.: 14/682,847

(22) Filed: Apr. 9, 2015

(65) Prior Publication Data
US 2016/0299041 A1    Oct. 13, 2016

(51) Int. Cl.
G01N 1/10    (2006.01)
G01N 1/24    (2006.01)
G01N 1/02    (2006.01)

(52) U.S. Cl.
CPC ............... G01N 1/24 (2013.01); G01N 1/10 (2013.01); G01N 2001/028 (2013.01)

(58) Field of Classification Search
CPC ....... G01N 1/24; G01N 1/10; G01N 2001/028
See application file for complete search history.

(56) References Cited

U.S. PATENT DOCUMENTS

| | | |
|---|---|---|
| 6,803,566 B2 | 10/2004 | Van Berkel |
| 7,525,105 B2 | 4/2009 | Kovtoun |
| 8,486,703 B2 | 7/2013 | Van Berkel et al. |
| 8,519,330 B2 | 8/2013 | Van Berkel et al. |
| 8,637,813 B2 | 1/2014 | Van Berkel et al. |
| 8,742,338 B2 | 6/2014 | Van Berkel et al. |
| 2005/0258361 A1 | 11/2005 | Whitehouse et al. |
| 2008/0128614 A1 | 6/2008 | Nikolaev et al. |
| 2010/0224013 A1 | 9/2010 | Van Berkel et al. |
| 2011/0198495 A1 | 8/2011 | Hiraoka |
| 2012/0079894 A1 | 4/2012 | Van Berkel et al. |
| 2014/0216177 A1 | 8/2014 | Van Berkel et al. |
| 2014/0238155 A1 | 8/2014 | Van Berkel et al. |

OTHER PUBLICATIONS

Ovchinnikova et al.: "Transmission geometry laser ablation into a non-contact liquid vortex probe for mass spectrometry imaging", Rapid Commun. Mass Spectrom. 2014, 28, 1665-1673.
International Search Report dated Jul. 1,2016 in PCT/US2016/026706.

Primary Examiner — Daniel S Larkin
Assistant Examiner — Anthony W Megna Fuentes
(74) Attorney, Agent, or Firm — Fox Rothschild LLP

(57) ABSTRACT

A system for sampling a sample material includes a device for directing sample into a capture probe. A probe includes an outer probe housing having an open end. A liquid supply conduit has an outlet positioned to deliver liquid to the open end. An exhaust conduit removes liquid from the open end of the housing. The liquid supply conduit can be connectable to a liquid supply for delivering liquid at a first volumetric flow rate to the open end of the housing. A liquid exhaust system can be in fluid connection with the liquid exhaust conduit for removing liquid from the liquid exhaust conduit at a second volumetric flow rate, which exceeds the first volumetric flow rate such that gas with sample is withdrawn with the liquid.

28 Claims, 20 Drawing Sheets

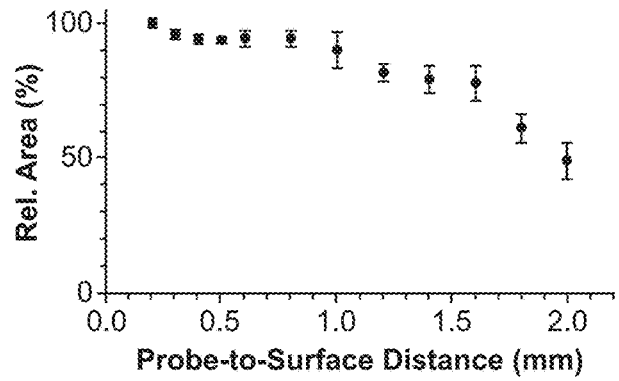
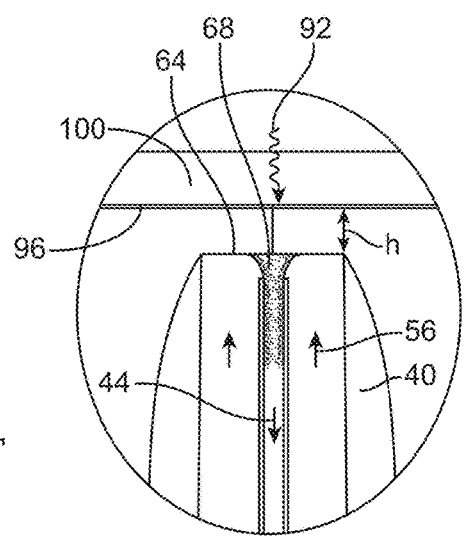
FIG. 3A           FIG. 3B
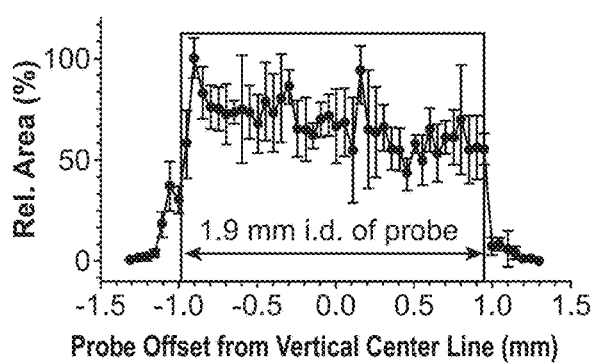
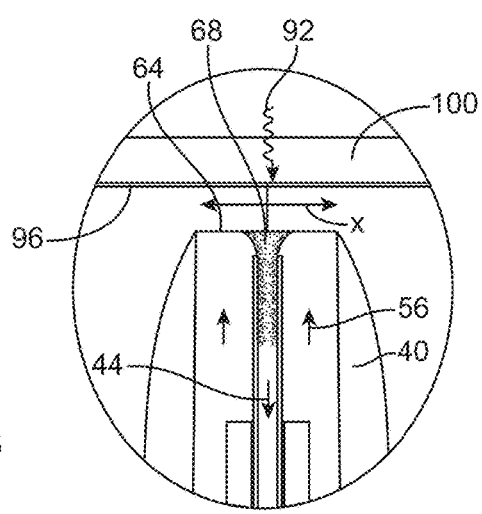
FIG. 4A           FIG. 4B

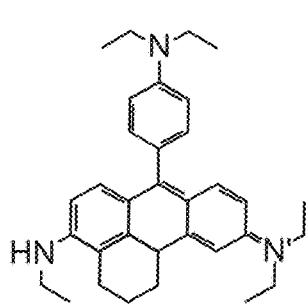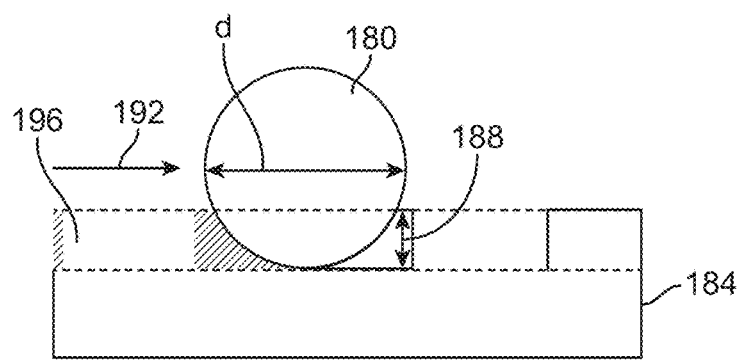
FIG. 6A     FIG. 6B
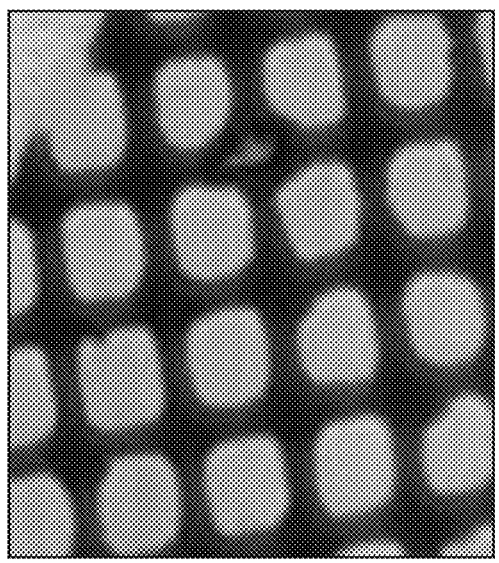
FIG. 6C     FIG. 6D

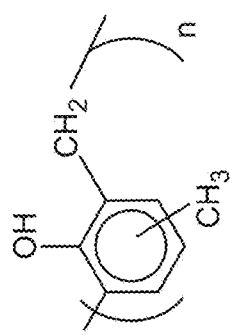
FIG. 10A
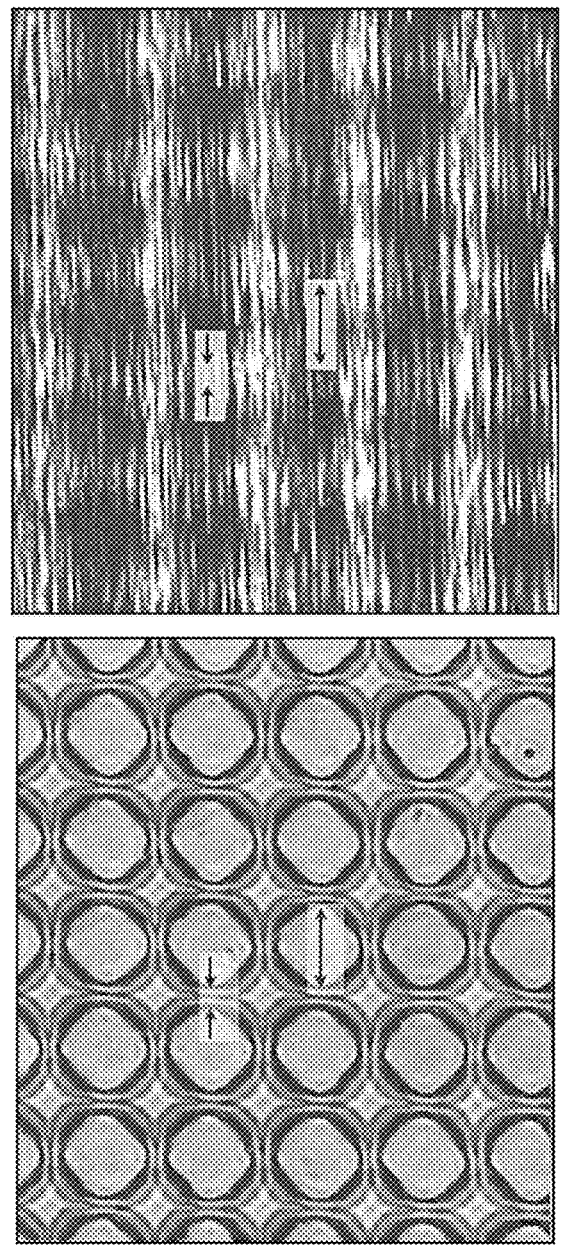
FIG. 10C
FIG. 10B

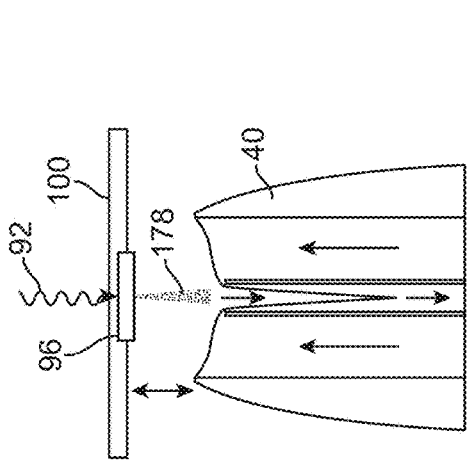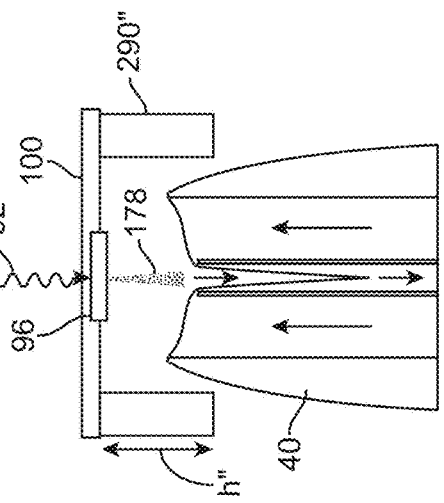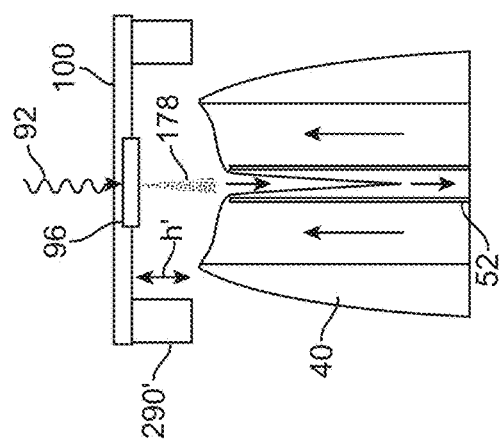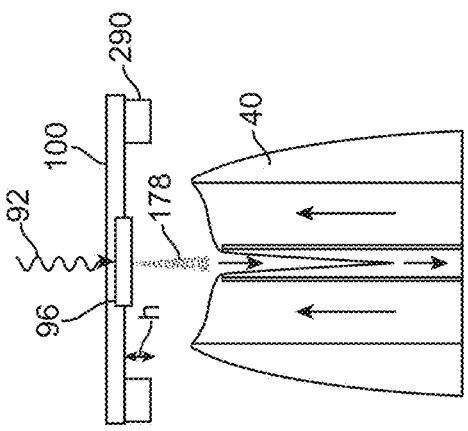

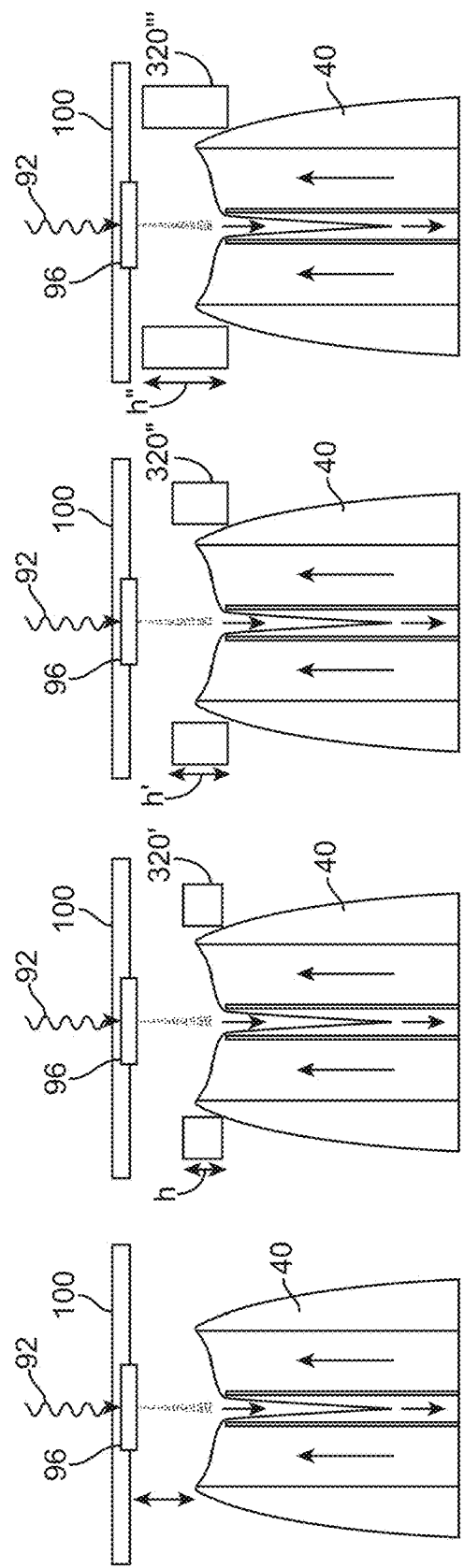

CAPTURE PROBE

STATEMENT REGARDING FEDERALLY SPONSORED RESEARCH

This invention was made with government support under contract No. DE-AC05-000R22725 awarded by the U.S. Department of Energy. The government has certain rights in this invention.

FIELD OF THE INVENTION

This invention relates generally to sample analysis systems and methods, and more particularly to sample analysis systems utilizing sampling probes.

BACKGROUND OF THE INVENTION

The capture of sample particulates and airborne sample material provides challenges with a liquid sampling probe, particularly in the case where sample material is first ejected from the sample by the application of radiant energy such as a laser beam or by acoustic desorption, or otherwise where there is a sample material that is airborne or otherwise ejected from a sample surface. The sample material if airborne can disperse before it is collected by the probe. An efficient liquid probe system for capturing such sample material would be desirable.

SUMMARY OF THE INVENTION

A system for sampling a sample material includes a device for supplying sample to a capture probe. The device for supplying sample material to the probe can be a device for radiating energy to the sample material to eject sample from the sample material. The system also includes a probe comprising an outer probe housing having an inner wall and an open end for communicating with a sample space. A liquid supply conduit is provided within the housing and has an outlet positioned to deliver liquid to the open end of the housing. An exhaust conduit is provided within the housing for removing liquid from the open end of the housing. The liquid supply conduit can be connectable to a liquid supply for delivering liquid at a first volumetric flow rate to the open end of the housing. A liquid exhaust system can be in fluid connection with the liquid exhaust conduit for removing liquid from the liquid exhaust conduit at a second volumetric flow rate. The second volumetric flow rate exceeds the first volumetric flow rate, whereby gas containing sample from the sample space will be withdrawn with liquid flowing through the liquid exhaust conduit. The probe can produce a vortex of liquid in the liquid exhaust conduit.

The device for radiating energy can be a laser producing a laser beam. The sample can be provided on a support that is transparent to the wavelength and the laser can be positioned to direct the laser beam through the support to the sample. The laser can be positioned on the same side of the support as the sample.

The second volumetric flow rate can exceed the first volumetric flow rate by at least 5%. The second volumetric flow rate can exceed the first volumetric flow rate by between 5-50%.

The system can further include a gas guide between the open end of the probe and the sample material for focusing the flow of gas into the liquid exhaust conduit.

A voltage source can be electrically connected to create a voltage difference between the sample material and the probe.

A method for sampling a sample material can include the step of providing a device for directing sample into a capture probe. The sample material can be positioned on a sample support. A radiation energy source can be provided for directing a beam of radiation at the sample material. A probe is provided having an open end. The open end can be positioned a distance from the sample and the sample support to define a sample space. Liquid can be supplied to the open end of the probe at a first volumetric flow rate. The liquid can be removed from the open end of the probe at a second volumetric flow rate, the second volumetric flow rate exceeding the first volumetric flow rate. The radiation energy source can be operated to eject sample material from the sample. The ejected sample material and gas from the sample space can be removed with the liquid removed from the open end of the probe. The removed liquid containing sample and gas can be subjected to chemical analysis. The liquid removed from the open end can form a vortex as it enters a liquid exhaust conduit.

The radiation energy can be a laser beam. The sample can be provided on a support that is transparent to the wavelength and the laser can be positioned to direct the laser beam through the support to the sample. The laser beam can emanate from the same side of the support as the sample.

The second volumetric flow rate can exceed the first volumetric flow rate by at least 5%. The second volumetric flow rate can exceed the first volumetric flow rate by between 5-50%.

The method can further include the step of providing a gas guide between the open end of the probe and the sample for focusing the flow of gas in the sample space and into the liquid exhaust conduit.

The method can further include the step of creating a voltage difference between the sample and the probe.

A sampling probe system can include an outer probe housing having an inner wall and an open end for communicating with a sample space, a liquid supply conduit within the housing and having an outlet positioned to deliver liquid to the open end of the housing, and an exhaust conduit within the housing for removing liquid from the open end of the housing. The liquid supply conduit can be connectable to a liquid supply for delivering liquid at a first volumetric flow rate to the open end of the housing. A liquid removal system can be in fluid connection with the liquid exhaust conduit for removing liquid from the liquid exhaust conduit at a second volumetric flow rate. The second volumetric flow rate exceeds the first volumetric flow rate, whereby gas containing sample from the sample space will be withdrawn with liquid flowing through the liquid exhaust conduit. The liquid can enter the liquid exhaust conduit as a vortex.

BRIEF DESCRIPTION OF THE DRAWINGS

There are shown in the drawings embodiments that are presently preferred it being understood that the invention is not limited to the arrangements and instrumentalities shown, wherein:

FIG. 2 is an enlarged schematic diagram of area A in FIG. 1.

FIG. 3 is FIG. 3A a plot of Rel. Area (%) vs. Probe-to-surface Distance (mm); and FIG. 3B a schematic diagram illustrating the distance h of the probe to the sample.

FIG. 4 is FIG. 4A a plot of Rel. Area (%) vs. Probe Offset from Vertical Center Line (mm); and FIG. 4B a schematic diagram illustrating the position x of the probe from the center line.

FIG. 6 is FIG. 6A a chemical structure diagram of the dye basic blue 7, present in blue permanent marker ink; FIG. 6B a schematic diagram illustrating the oversampling methodology; FIG. 6C an optical image of stamped blue ink grid pattern; and FIG. 6D a chemical image of basic blue 7 from the same stamped ink pattern.

FIG. 10 is FIG. 10A a chemical structure for Novolac resin; FIG. 10B an optical image for a second photoresist pattern formed from Novolac resin; and FIG. 10C a chemical image of the chemical components of the Novolac resin from the same portion of the this second photoresist pattern.

FIG. 16 is FIG. 16A a cross section of a plume-focusing gas guide; FIG. 16B is a vertical cross section; FIG. 16C no plume-gas focusing guide; FIG. 16D a gas guide having first height h; FIG. 16E a gas guide having a second height h'; and FIG. 16F a gas guide having a third height h".

FIG. 18 is FIG. 18A a cross section of a plume-focusing gas guide that is detached from the sample support; FIG. 18B a schematic diagram illustrating guide wall height; schematic diagrams of FIG. 18C no plume-gas focusing guide; FIG. 18D a gas guide having first height h; FIG. 18E a gas guide having a second height h'; and FIG. 18F a gas guide having a third height h".

FIG. 20B an enlarged area B; and FIG. 20C a depiction of liquid and gas flow into the probe.

DETAILED DESCRIPTION OF THE INVENTION

Figure 1:
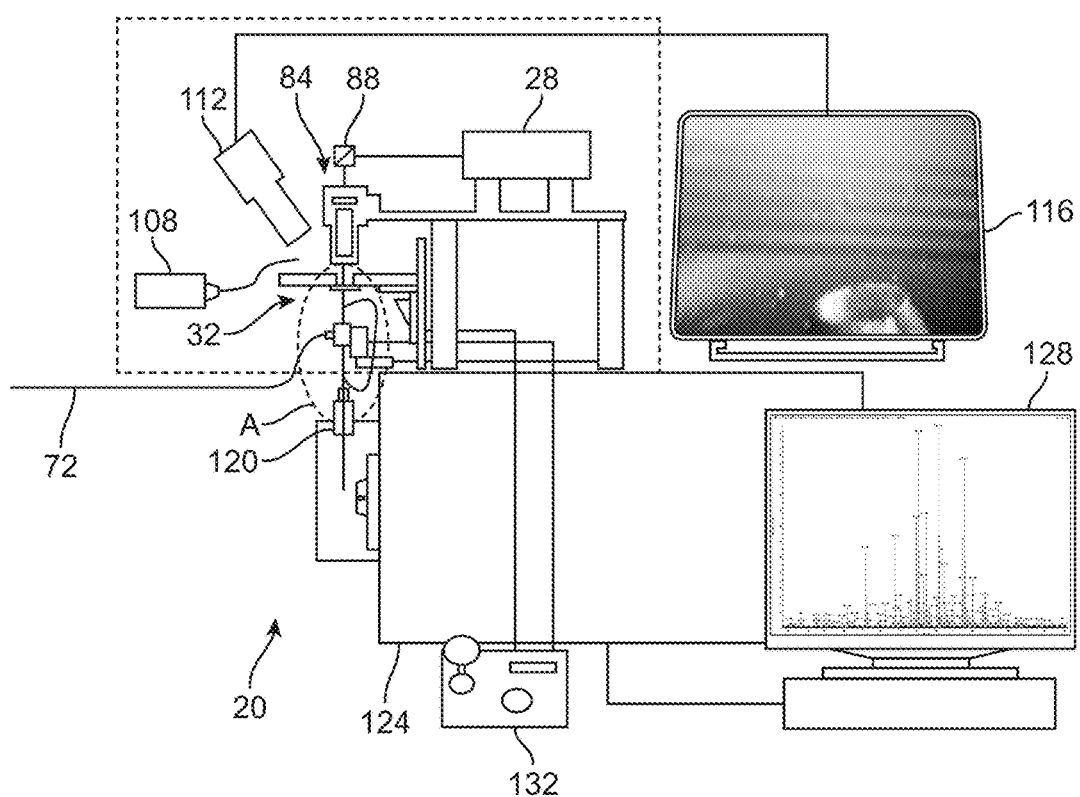
FIG. 1 is a schematic diagram of a system for sampling a surface.
Figures 2A, 2B:
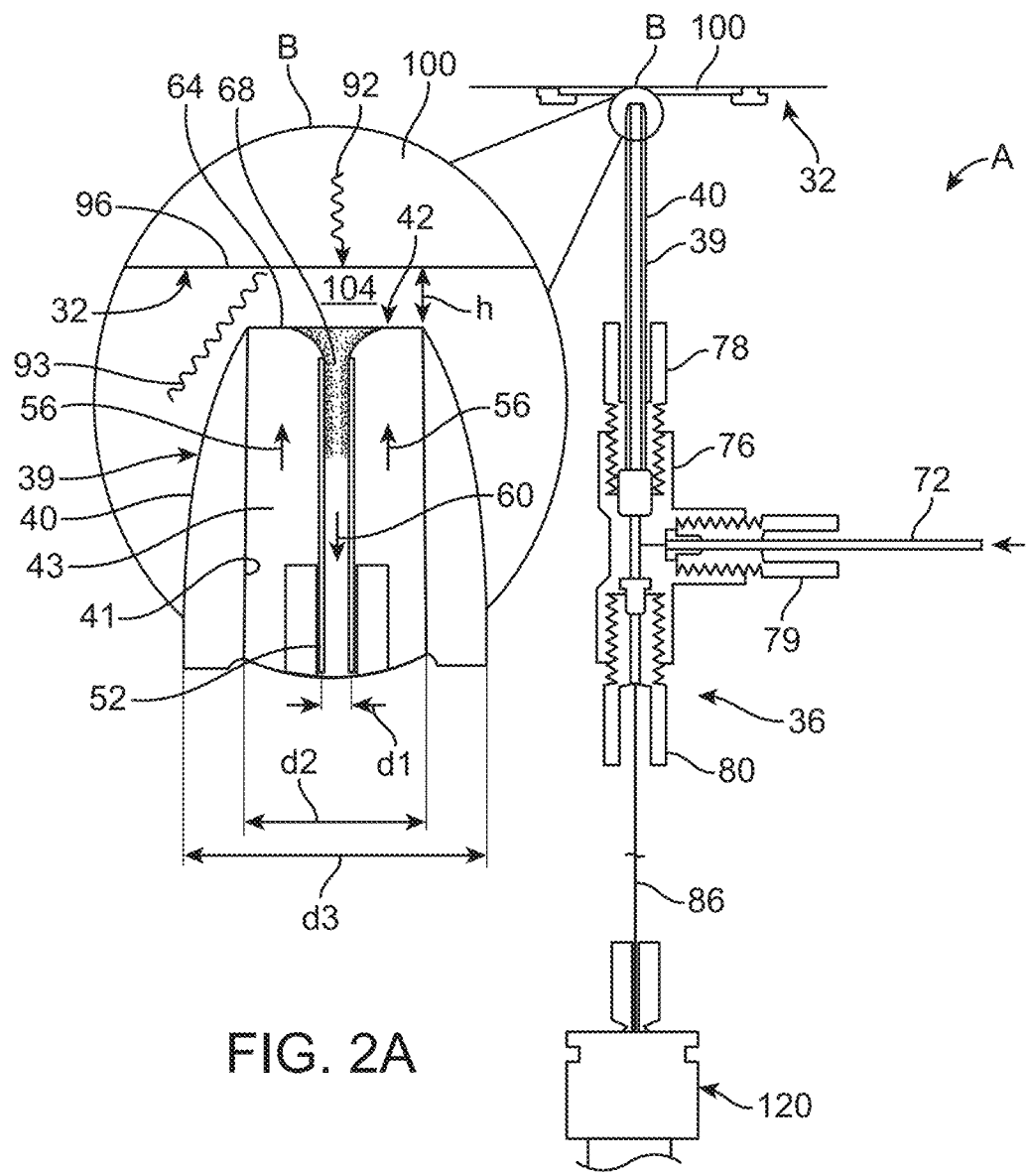
FIG. 2A is an enlarged schematic diagram of area B in FIG. 2.

FIG. 1-2 are schematic diagrams of a system for sampling a surface. There is shown in the figures a system 20 for sampling a sample area 32 including a sample surface 96 which includes a device 28 for radiating energy to the surface 96 to eject sample from the sample material. The invention can be utilized with many different systems and methods for generating sample material and directing the sample material into or toward the probe. The probe is shown in a vertical orientation, but can also be used in other orientations. The system also includes a probe 39 comprising an outer probe housing 40 having an inner wall 41 and an open end 42 for communicating with a sample space 104. A liquid supply conduit 43 is provided within the housing and has an outlet positioned to deliver liquid to the open end of the housing. An exhaust conduit 52 is provided within the housing 40 for removing liquid from the open end 68 of the exhaust conduit 52. The position of the open end 68 relative to the open end 42 of the probe can vary to adjust flow conditions into the exhaust conduit 52. The liquid supply conduit can be an annular space between the exhaust conduit 52 and the inner wall 41 of the housing 40. Other configurations are possible for delivering solvent to the open end of the housing, for example, one or more tubular liquid supply conduits.

The liquid supply conduit can be connectable to a liquid supply such as intake line 72 for delivering liquid as shown by arrow 56 at a first volumetric flow rate to the open end 42 of the housing 40. A liquid exhaust system can be in fluid connection with the liquid exhaust conduit 52 for removing liquid as shown by arrow 60 from the liquid exhaust conduit 52 at a second volumetric flow rate. The second volumetric flow rate exceeds the first volumetric flow rate, whereby gas containing sample from the sample space 104 will be withdrawn with liquid flowing through the liquid exhaust conduit 52. The probe 39 can produce a vortex 45 of liquid in the liquid exhaust conduit 52 as shown, although a vortex is not necessary for functioning of the device. The relative diameters of the liquid exhaust conduit 52 $d_1$, the liquid supply conduit 43 $d_2$ and the outer diameter of the probe 39 $d_3$ can vary. The distance between the sample and liquid surface 64 can vary, as indicated by the arrows h in FIG. 2A. The distance from the inlet of the liquid exhaust conduit 52 and the open end 42 of the housing 40 can also vary.

The excess of volume leaving the liquid exhaust conduit 52 at the second volumetric flow rate relative to the amount of liquid entering the probe at the first volumetric flow rate results at the entrance to the liquid exhaust conduit 52 in the draw of gas from the sample space 104 into the liquid exhaust conduit 52. Positioning of the open end 42 below the sample 96 at the point where radiant energy strikes the sample 96 will cause sample material to fall or otherwise be ejected toward the liquid surface 64. Liquid including the captured sample material will enter the liquid exhaust conduit 52 and thereby collected for further analysis. Airborne sample material ejected from the sample will be assisted to the center of the liquid exhaust conduit 52 by gas flow created by the greater volumetric flow of liquid out of the probe 39 through the exhaust conduit 52 than into the probe 39 through the supply conduit 43.

The amount by which the second volumetric flow rate exceeds the first volumetric flow rate can vary, and will in part depend upon the characteristics of the sample, liquid, and probe size and geometry. In one embodiment, the second volumetric flow rate can exceed the first volumetric flow rate by at least 5%. In another embodiment the second volumetric flow rate can exceed the first volumetric flow rate by between 5-50%.

The device 28 for directing sample into the capture probe 39 can be a laser radiating energy such as a laser beam 92. The device for radiating energy can radiate intense heat. The wavelength and intensity of the energy can vary based upon the characteristics of the sample being tested. The sample 96 can be provided on a support 100. The support 100 can be transparent to the wavelength of the radiated energy such that the laser 28 can be positioned to direct the laser beam 92 through the support to the sample 96. The laser 28 can be positioned on the same side of the support 100 as the sample 96 such that a laser beam 93 emanates directly at the sample 96 without passing through the support 100. The device for directing sample into the capture probe can be an acoustic desorption device wherein a laser or other energy imparting device is used to generate an acoustic wave which travels through the sample support to impart energy to the sample and eject sample material from the sample. The acoustic desorption can be laser induced acoustic desorption. The invention can be used with other means for ejecting sample material from the sample to the probe, and many other devices and methods for directing sample into the capture probe.

The system 20 can deliver to and remove solvent from the probe 39 by any suitable means. The liquid intake line 72 receives liquid from a suitable source such as a container or a liquid supply line. A pump such as an HPLC pump (not shown) can be used to meter solvent flow into the probe 39. The liquid can be any suitable solvent for the sample material, such as water, methanol, or acetonitrile. Other solvents are possible. A T-connection 76 can include a fitting 78 to engage the probe 39 and make a fluid connection with fitting 79 and between the liquid supply line 72 and the liquid supply conduit 43. A fitting 80 can make a connection between the liquid exhaust conduit 52 and the liquid exhaust line 86. The exhaust line 86 can be connected to inlet 120 of a chemical analysis device such as a mass spectrometer. Other connection materials and methods are possible.

The system 20 can have other features. A 90 degree prism 88 can be provided to direct the laser beam through a microscope objective 84. A light source 108 can be provided. A video monitor 116 can be provided. A mass spectrometer 124 or other chemical analysis device can be provided and can have a monitor 128 and a suitable control 132 joystick or other control device.

FIG. 3 is FIG. 3A a plot of Rel. Area (%) vs. Probe-to-surface Distance (mm); and FIG. 3B a schematic diagram illustrating the distance h of the probe to the sample. FIG. 3A illustrates that capture of material ejected from the surface is relatively constant to a 1.5 mm spacing.

FIG. 4 is FIG. 4A a plot of Rel. Area (%) vs. Probe Offset from Vertical Center Line (mm); and FIG. 4B a schematic diagram illustrating the position x of the probe from the center line. The plot of FIG. 4A illustrates that capture of material ejected from the surface is relatively stable with probe movement illustrated by arrow x in FIG. 4B up to 1 mm from the vertical center line. In this embodiment gravity helps to direct ablated material down towards the capture liquid.

Figure 5A:
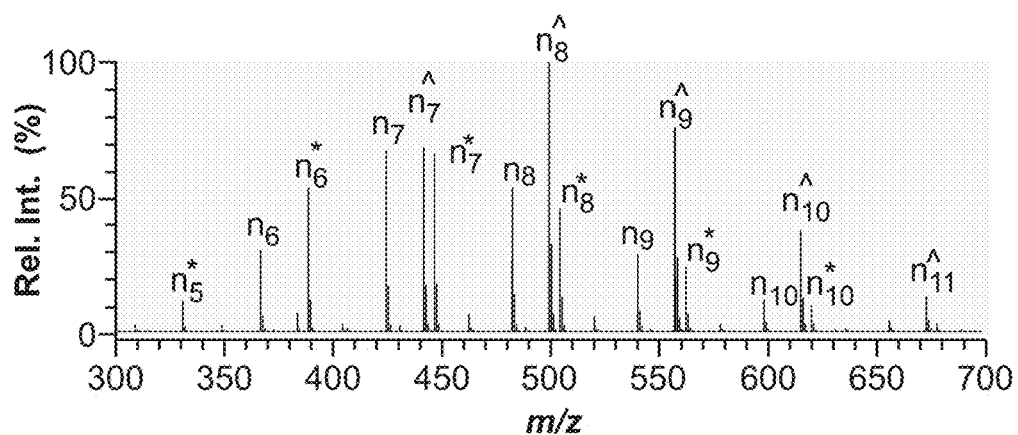
FIG. 5 is a plot of mass to charge (m/z) ratio vs. Rel. Int. (%) for FIG. 5A polypropylene glycol.
FIG. 5B bovine insulin side chain B.
FIG. 5C horse heart cytochrome c.
Figure 5B:
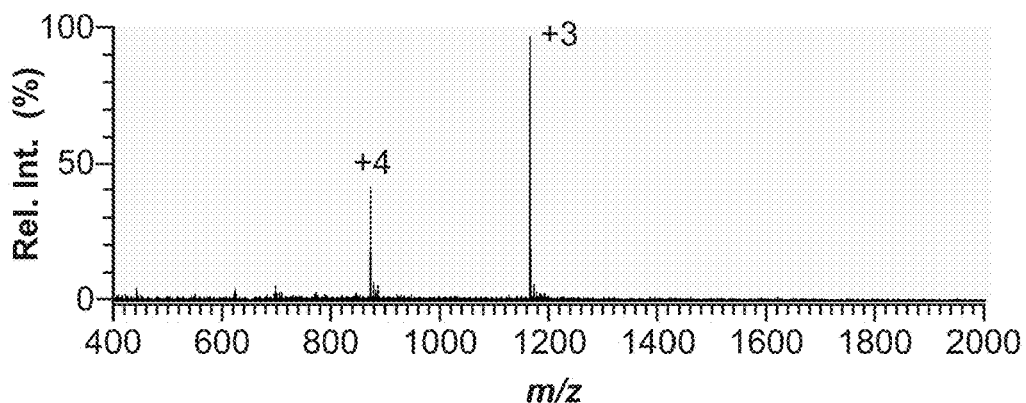
Figure 5C:
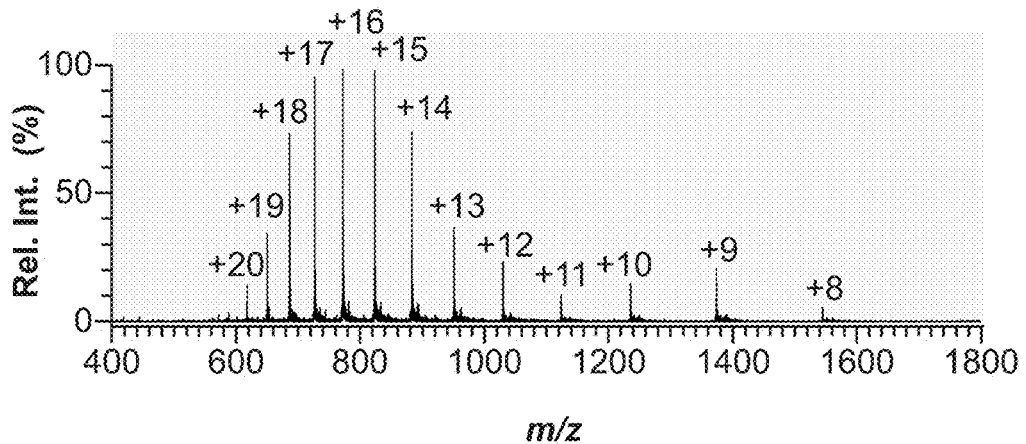

FIG. 5 is a plot of mass to charge (m/z) vs. Rel. Int. (%) for FIG. 5A polypropylene glycol; FIG. 5B bovine insulin side chain B; and FIG. 5C horse heart cytochrome c obtained using positive ion mode electrospray ionization mass spectrometry for detection. FIG. 5A is the result of the analysis of a propylene glycol mixture containing PPG 425—0.1 nmole spotted on a Director® slide. The capture solvent was 80/20/0.1 (v/v/v) methanol/water/formic acid at 200 μL/min. FIG. 5B is the result for the analysis of bovine insulin side chain B (3494 Da)—0.3 nmol spotted on a Director® slide. The capture solvent was 50/50/0.1 (v/v/v) acetonitrile/water/formic acid flowing at 200 μL/min. FIG. 5C is the result for horse heart cytochrome c (12360.2 Da)—81 μmol spotted on a Director® slide. These mass spectra illustrate that with this system a wide variety of organic and biological molecules can be ejected from the surface using a laser, captured in a liquid, ionized and mass analyzed, with the molecules remaining intact.

Testing of the chemical imaging capability of this system was performed using a stamped ink grid containing the dye basic blue 7 (m/z 478 having the chemical structure shown in FIG. 6A). There is shown in FIG. 6B a schematic diagram illustrating a sampling methodology termed oversampling, where the laser spot 180 is scanned over an incremental step 188 on ink line 184 in the direction of arrow 192 leaving a sampled area 196. The laser spot size d was 50 μm, the surface scan speed 10 μm/s, with 2.5 μm steps between lanes and 51 lane scans. Capture liquid flow was methanol+0.1% formic acid at 200 μL/min. Analysis was performed with AB Sciex Triple TOF 5600+, full scan m/z 100-1000 using positive ion mode electrospray ionization, 250 ms acquisition time. A 355 nm Nd:YAG laser was used at 10 Hz, 60 μJ/pulse. The chemical image shown in FIG. 6D correlates well with the optical image shown in FIG. 6C. The pixel size was 2.5 μm×2.5 μm.

Figure 7A:
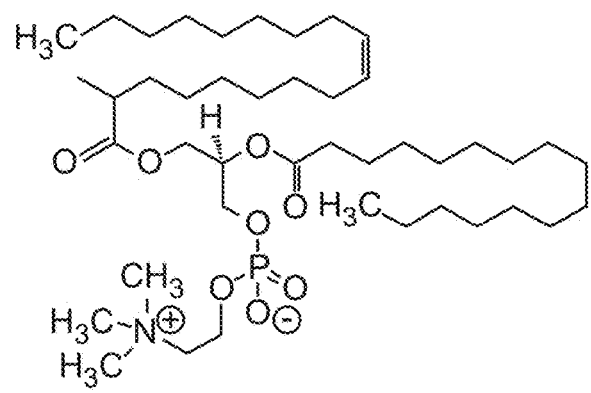
FIG. 7 is FIG. 7A a chemical structure diagram of phosphatidylcholine lipid.
FIG. 7B an optical image of a portion of a small animal brain thin section.
FIG. 7C a chemical image of the phosphatidylcholine lipid from the same portion of the thin section.
Figures 7B, 7C:
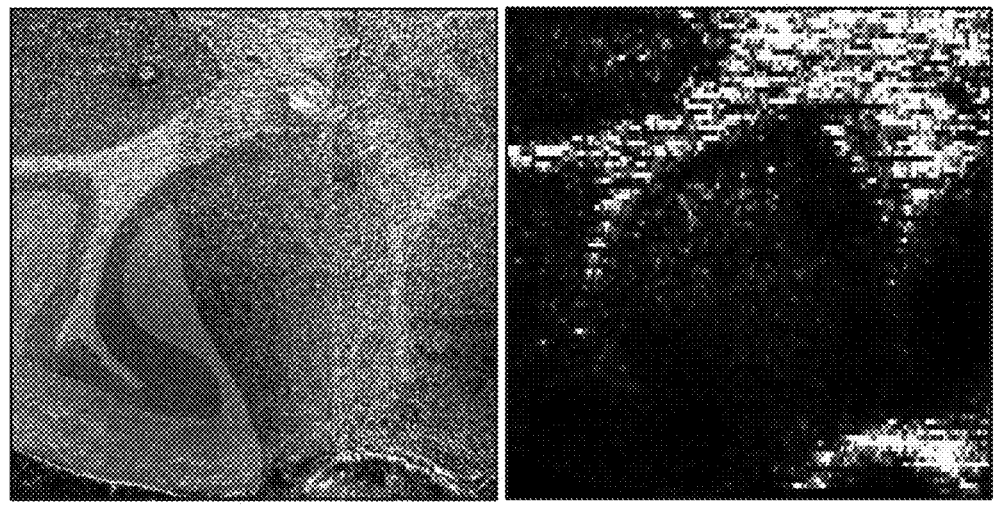

There is shown in FIG. 7A a chemical structure diagram of the phosphatidylcholine lipid from mouse brain detected using a selected reaction monitoring tandem mass spectrometry mode to improve detection selectivity. The mouse brain tissue was placed on a PEN 1.0 slide. The laser spot was 50 μm. The acquisition parameters were 50 μm/s and 20 μm steps with 151 lanes. Solvent flow was 200 μL/min, methanol+0.1% formic acid. Analysis was performed with AB Sciex Triple TOF 5600+, using positive ion mode electrospray ionization product ion m/z 760.6→184.06 (CE=45 eV), 250 ms acquisition time. A 355 nm Nd:YAG laser was used at 10 Hz, 60 μJ/pulse. The chemical image shown in FIG. 7C correlates well with the optical image shown in FIG. 7B. The image pixel size was 12 μm×20 μm.

Figure 8A:
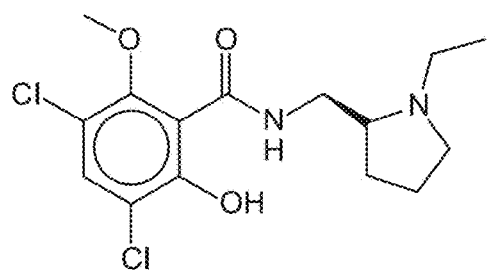
FIG. 8 is FIG. 8A a chemical structure diagram of raclopride.
FIG. 8B an optical image of a small animal brain thin section.
FIG. 8C an enlarged optical image of the thin section.
FIG. 8D a chemical image of raclopride from the same portion of the thin section.
Figure 8B:
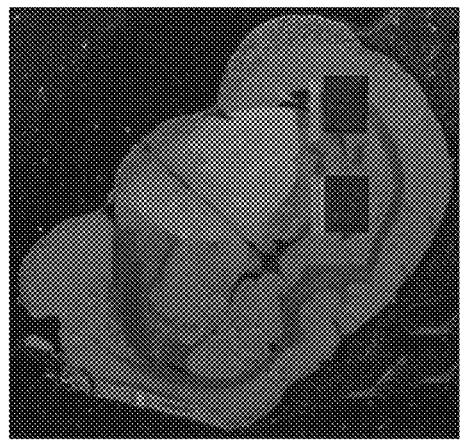
Figure 8C:
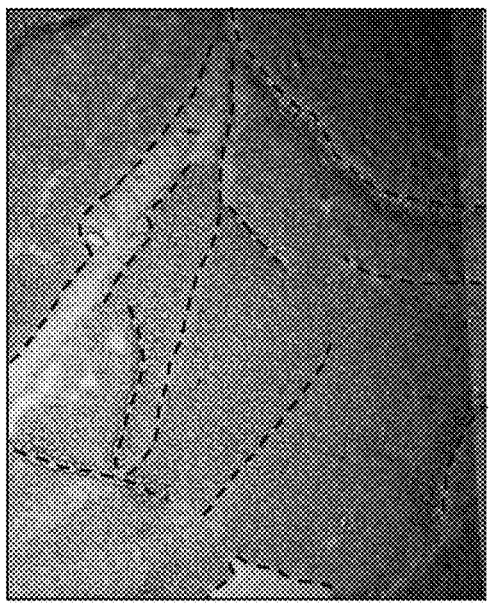
Figure 8D:
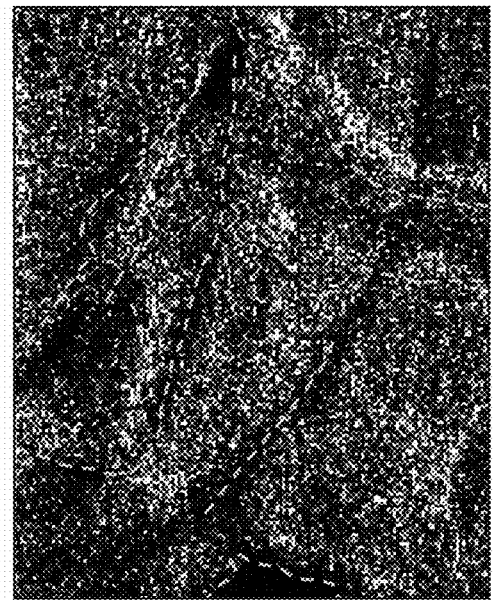

There is shown in FIG. 8A a chemical structure diagram of raclopride. Raclopride has a high affinity for dopamine D-2 receptors in rat brain. Rats were IV-dosed with 2 mg/kg raclopride and sacrificed 5 minutes post dose. The excised brain was flash frozen, sectioned at 6 μm thick, and thaw mounted on PEN 1.0 slides. The imaging was performed on 9 μm×10 μm pixels, with a 12×10 μm laser spot. The acquisition parameters were 40 μm/s and 10 μm steps with 151 lanes. Solvent flow was 200 μL/min, methanol+0.1% formic acid. Analysis was performed with AB Sciex Triple TOF 5600+, using positive ion mode electrospray ionization and selected reaction monitoring m/z 347.1→112 (CE=45 eV), 250 ms acquisition time. A 355 nm Nd:YAG laser was used at 10 Hz, 60 µJ/pulse. The chemical image shown in FIG. 8D correlates well with the optical image shown in FIG. 8C.

Figure 9A:
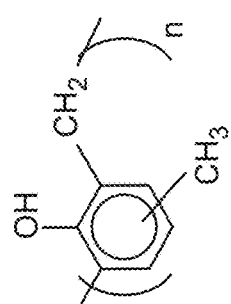
FIG. 9 is FIG. 9A a chemical structure diagram for Novolac resin.
FIG. 9B an optical image of a photoresist pattern formed from Novolac resin.
FIG. 9C a chemical image of the chemical components of the Novolac resin from the same portion of the photoresist pattern.
Figure 9C:
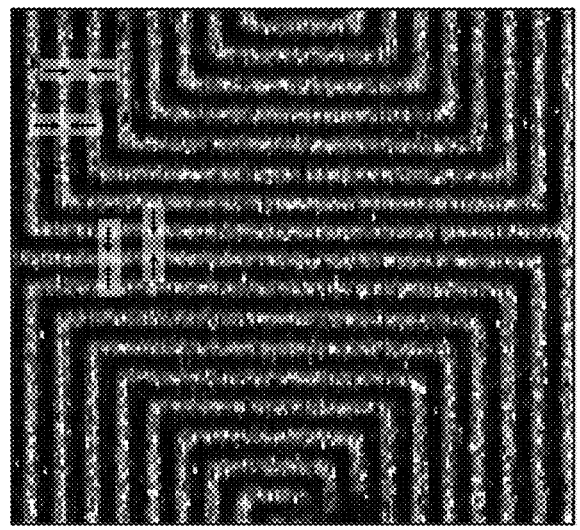
Figure 9B:
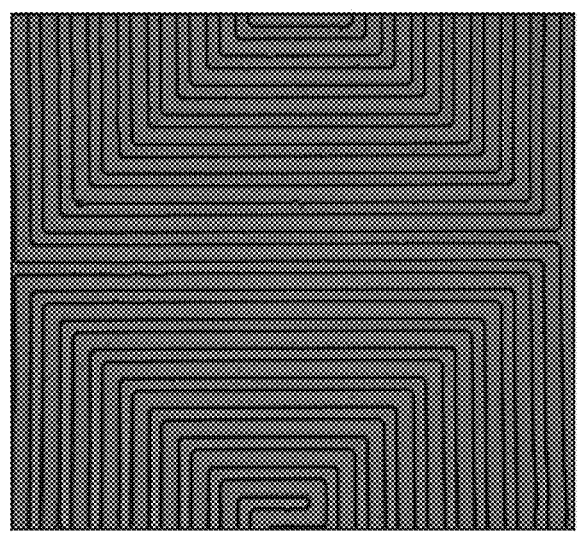

There is shown in FIG. 9A a chemical structure diagram for Novolac resin, having a 120 Da monomer unit. The experiment was performed on Novolac resin developed positive photoresist (1.5 µm thick) on glass. A 355 nm Nd:YAG laser was used at 10 Hz, 25 µJ/pulse. Analysis was performed by AB Sciex 5500 using negative ion mode electrospray ionization and selected reaction monitoring (m/z 227.2→107.2 (CE=30 eV), 50 ms dwell time). The surface scan speed was 6.7 µm/s, with 2.5 µm/lane step and 17 µm ablation spot. Solvent flow was 200 µL/min methanol. The total acquisition time was 4.5 h. The chemical image shown if FIG. 9C correlates well with the optical image shown in FIG. 9B. The pixel size was 2.5 µm×2.5 µm.

There is shown in FIG. 10A the chemical structure for Novolac resin; Solvent flow was 200 µL/min methanol. A 355 nm Nd:YAG laser was used at 10 Hz, 25 µJ/pulse. Analysis was performed by AB Sciex 5500 using negative ion mode electrospray ionization and selected reaction monitoring (m/z 227.2→107.2 (CE=30 eV), 50 ms dwell time). The scan speed was 6.7 µm/s, with 0.5 µm/lane step and 17 µm ablation spot. Solvent flow was 200 µL/min methanol. The total acquisition time was 2 h. The chemical image shown in FIG. 10C correlates well with the optical image shown in FIG. 10B. The pixel size was 0.5 µm×0.5 µm.

Figure 11:
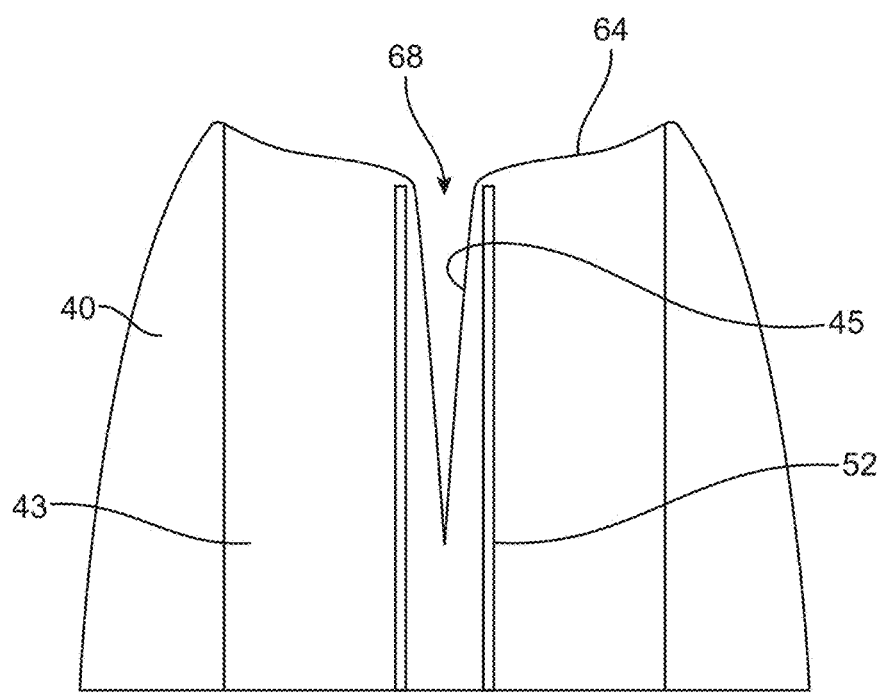
FIG. 11 is a schematic diagram of a probe with vortex liquid flow.

FIG. 11 is a schematic diagram of a probe and liquid vortex within. Liquid supplied through the liquid supply conduit 43 forms a liquid surface 64 at the open end of the probe 40. The liquid surface 64 captures sample material that has been ejected from the sample by the radiant energy or other sample introduction method. The over aspiration of liquid through the liquid exhaust conduit 52 relative to the volumetric flow rate of liquid through the liquid supply conduit 43 draws gas containing airborne sample material from space 68 into the liquid exhaust conduit. Depending on the liquid flow and geometry a vortex 45 can be formed by liquid flowing into the liquid exhaust conduit.

Figure 12:
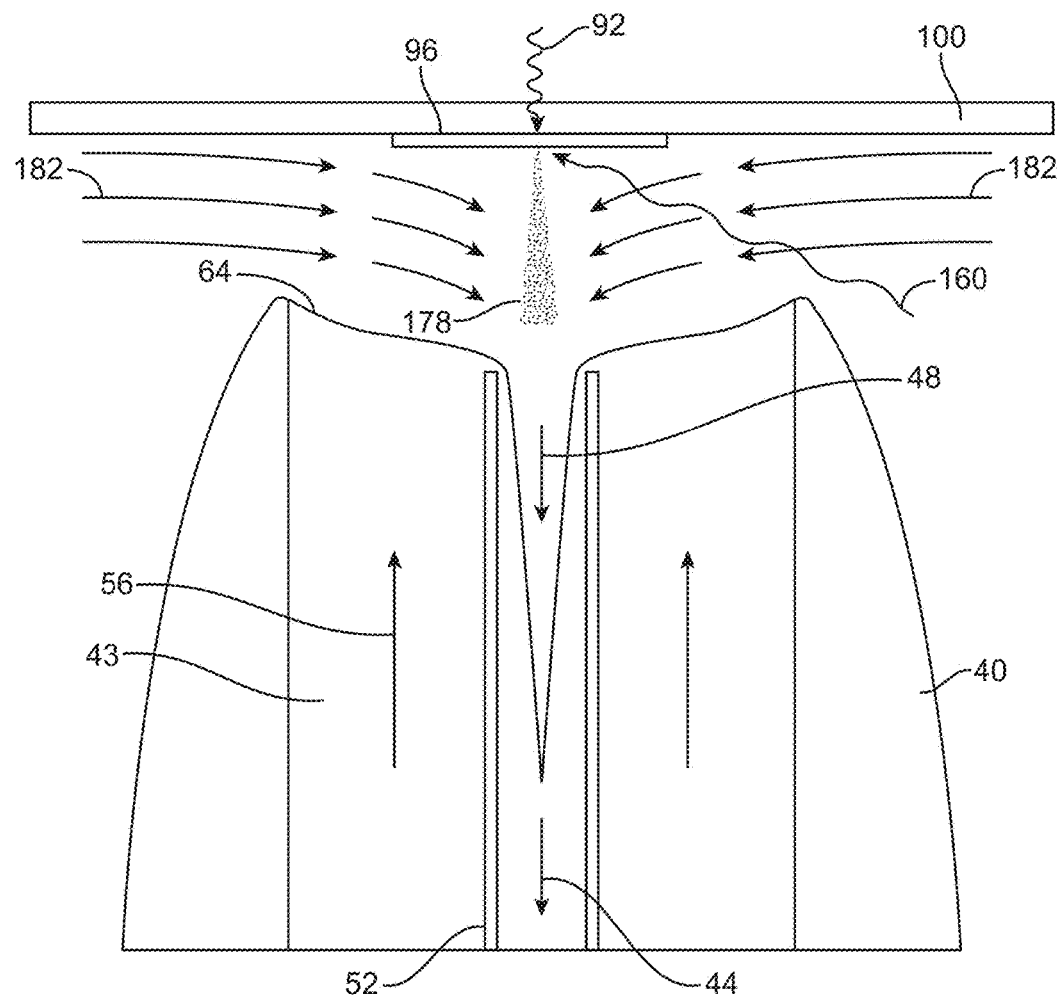
FIG. 12 is a schematic diagram of a probe with plume-focusing gas flow.
Figure 13:
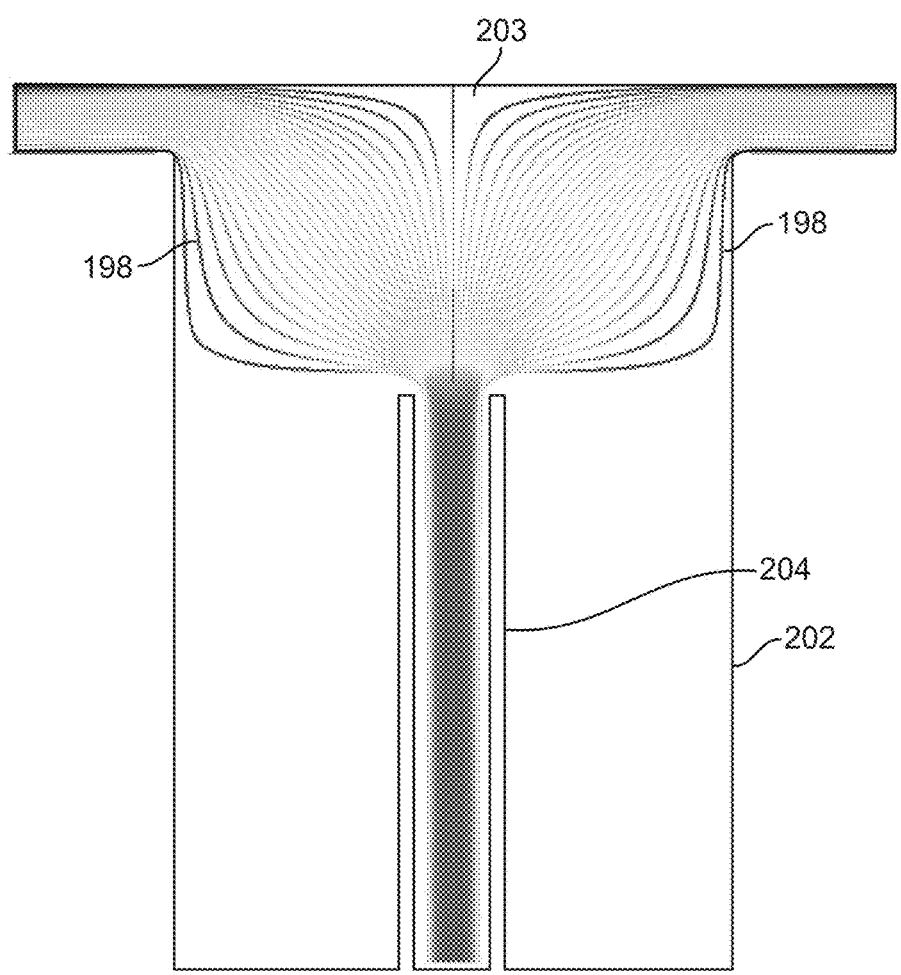
FIG. 13 is a diagram illustrating computer model results for gas flow into the exhaust conduit of a probe.

FIG. 12 is a schematic diagram of a probe with plume-focusing gas flow. Radiant energy such as laser beam 92 in transmission mode, or beam 160 in reflection mode from the same side of the support 100 as the sample 96, strikes the sample 96 and creates a plume 178 of ejected sample material, which can be particulates, gaseous species or other airborne material. Gas flow 182 drawn from the ambient environment by the probe flows generally radially inward toward the plume 178 to focus the plume and direct particulates and gas into the surface 64 and into the liquid exhaust conduit 52 in the direction of arrow 48. The precise direction and extent of focusing gas flow can vary depending on system geometry and operating characteristics. The ambient focusing gas can be air or another gas. FIG. 13 is a diagram illustrating computer model results for focusing gas flow 198 into the modeled exhaust conduit 204 of a probe 202. The model illustrates how the focusing gas guides the sample plume into a center space 203 and then into the exhaust conduit 204.

Figure 14A:
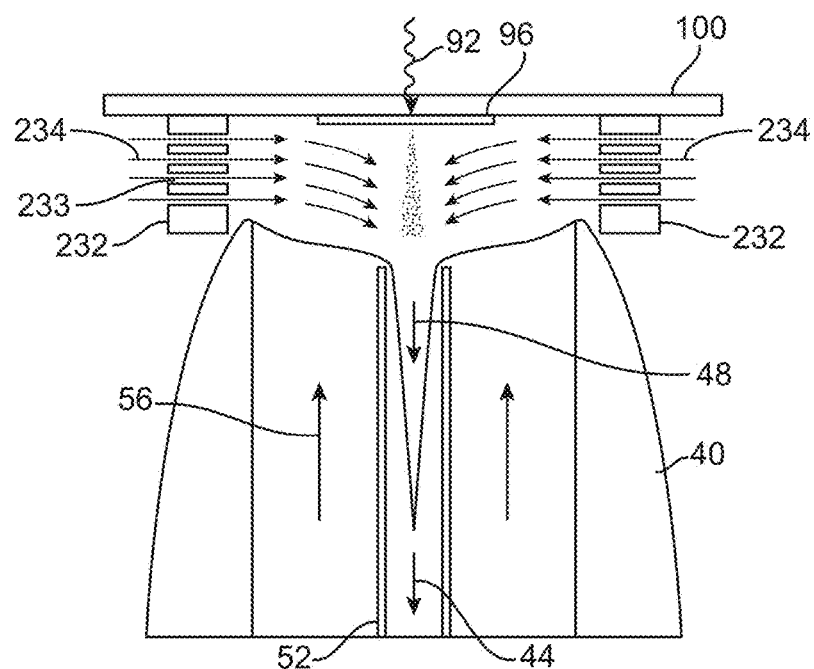
FIG. 14 is FIG. 14A a schematic diagram of a system with a plume-focusing gas guide spaced between the sample support and the probe.
FIG. 14B a cross section of the gas guide in a first focusing gas flow port configuration.
FIG. 14C a cross section of the gas guide in a second focusing gas flow port configuration.
Figure 14B:
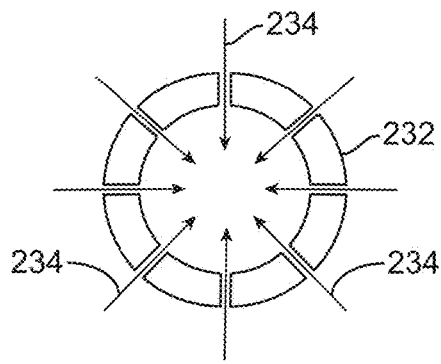
Figure 14C:
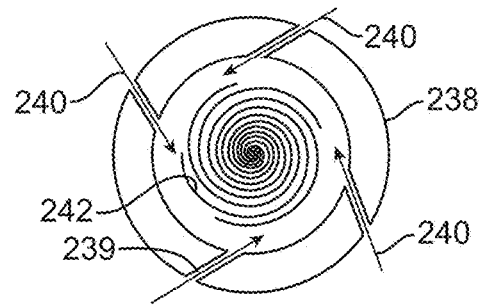

FIG. 14A is a schematic diagram of a system with a plume-focusing gas guide 232 spaced between the probe 40 and sample support 100. The gas guide 232 has a series of apertures 233 to direct focusing gas flow 234 radially inward. FIG. 14B is a cross section of the gas guide 232 showing the radially inward focusing gas flow 234. FIG. 14C is a cross section of an alternative gas guide 238 in a second focusing gas flow port configuration in which more tangentially oriented guide ports 239 are provided and direct focusing gas flow 240 in a cyclonic pattern so as to create gas vortex 242.

Figure 15A:
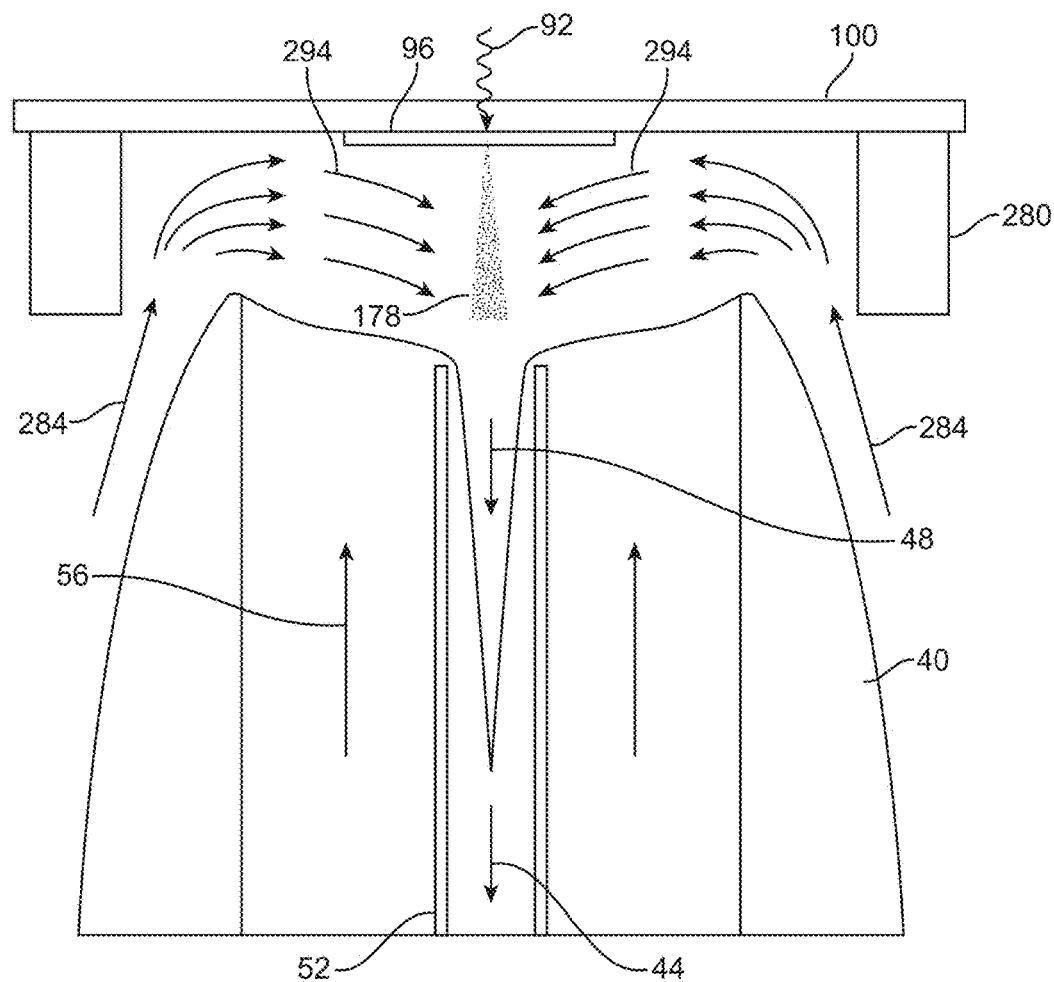
FIG. 15 is FIG. 15A a schematic diagram of a system with a plume-focusing gas guide in a baffle configuration.
FIG. 15B a cross section of the gas guide.
Figure 15B:
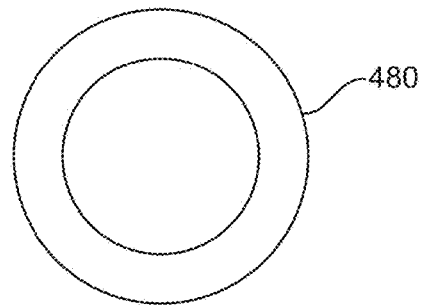

FIG. 15A-15B is a schematic diagram of a system with a plume-focusing gas guide 280 in a baffle configuration and connected to the support 100. Focusing gas 284 flows under the baffle guide 280 where it contacts the support 100 and is directed radially inward as illustrated by arrows 294.

FIG. 16A-16F illustrates a plume-focusing gas guide baffle 290 with a variety of heights. FIG. 16C illustrates the case of no baffle guide, and FIG. 16D-16F illustrates baffles guides 290, 290', and 290" which have a respectively greater height h.

Figure 17A:
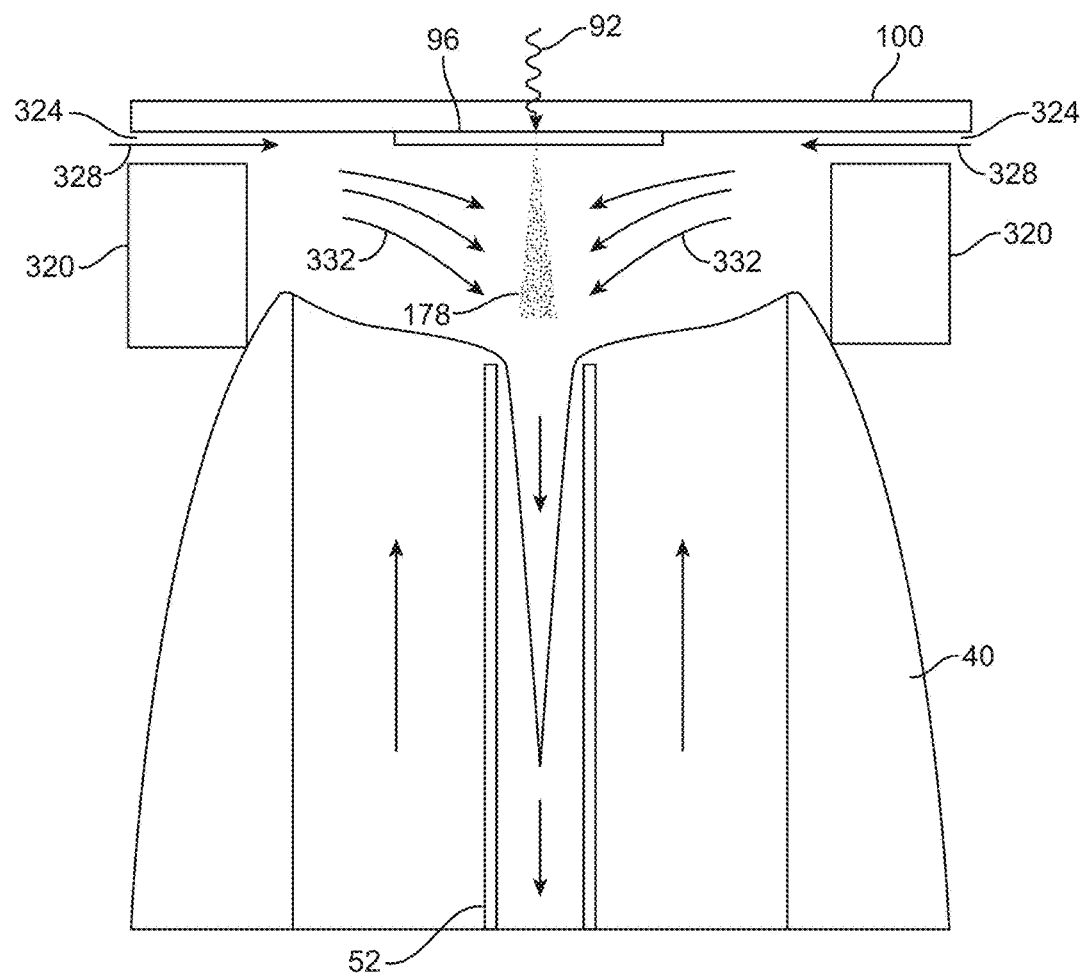
FIG. 17 is FIG. 17A a schematic diagram of a system with a plume-focusing gas guide that is separated from the sample support.
FIG. 17B a cross section of the gas guide.
Figure 17B:
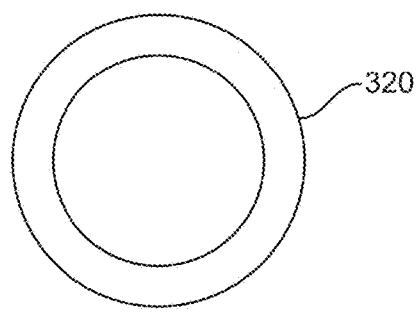

FIG. 17A-17B a schematic diagram of a system with a plume-focusing gas guide 320 that is separated from the sample support 100. The detached position of the gas guide 320 creates a circumferential channel 324 through which radially inwardly directed focusing gas flow 328 can pass, where it moves in flow 332 toward the liquid exhaust conduit 52. FIG. 18A-18F illustrates the plume-focusing gas guide 320 at a variety of different heights h, including the case with no gas guide.

Figure 19:
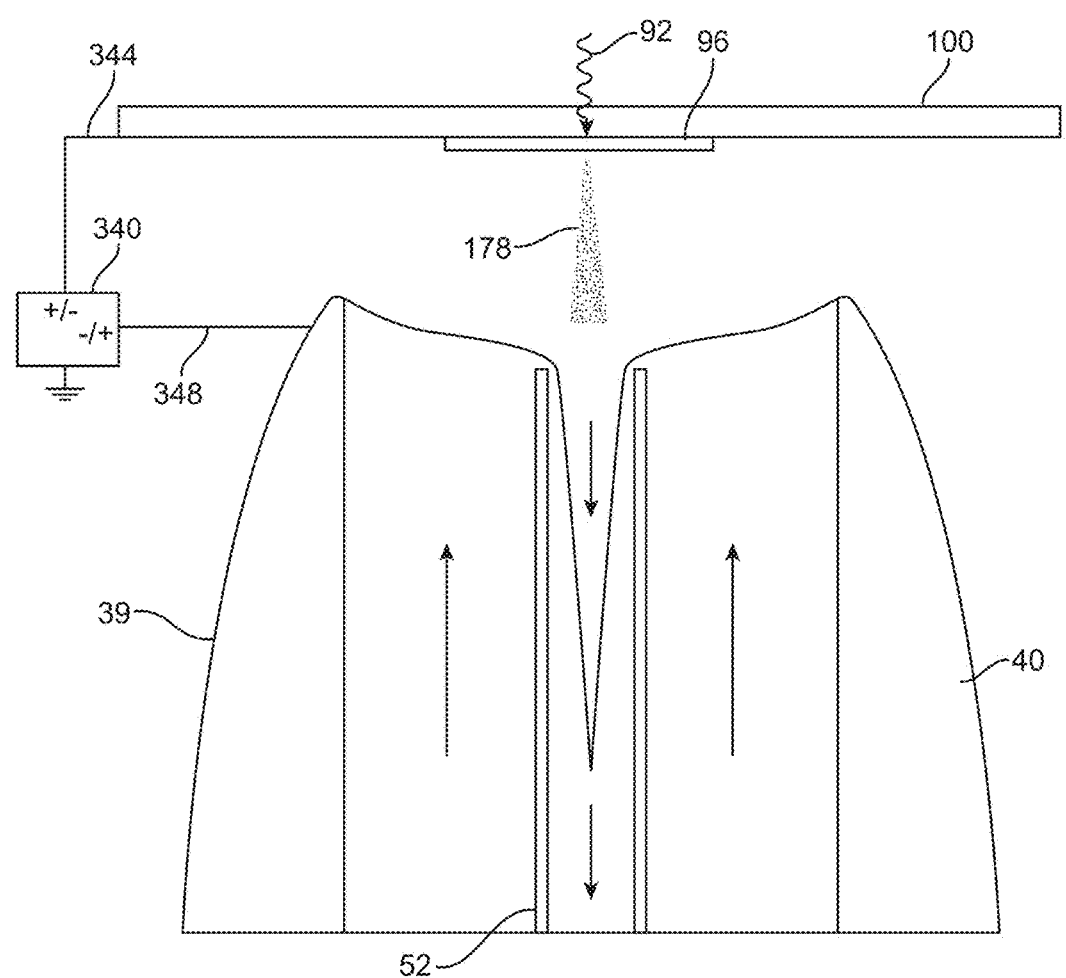
FIG. 19 is a schematic diagram of a system enabling a voltage difference to be applied between the sample and probe.

FIG. 19 is a schematic diagram of a system with a voltage-applying source 340 and electrical connections 344 to the support 100 and 348 to the probe 39. The application of a voltage difference will assist in the transport of charged components in the plume 178 to the probe 39. The voltage difference that can be applied can vary.

FIG. 20A is a schematic diagram of a system 400 for sampling a surface. The system 400 has a base unit 402 having a probe 39 and liquid supply and exhaust assembly as previously describe and illustrated by area C and FIG. 20B. A camera 112 and eyepiece 412 can be provided. A UV shield 416 can also be provided. A commercial laser microdissection system such as the LMD 7000 from Leica can be used and has an optical bright field and fluorescent microscope in addition to laser ablation capability. Other systems and configurations are possible to generate sample and direct it toward and into the probe. FIG. 20C illustrates vortex flow at the open end of the probe.

Figure 21:
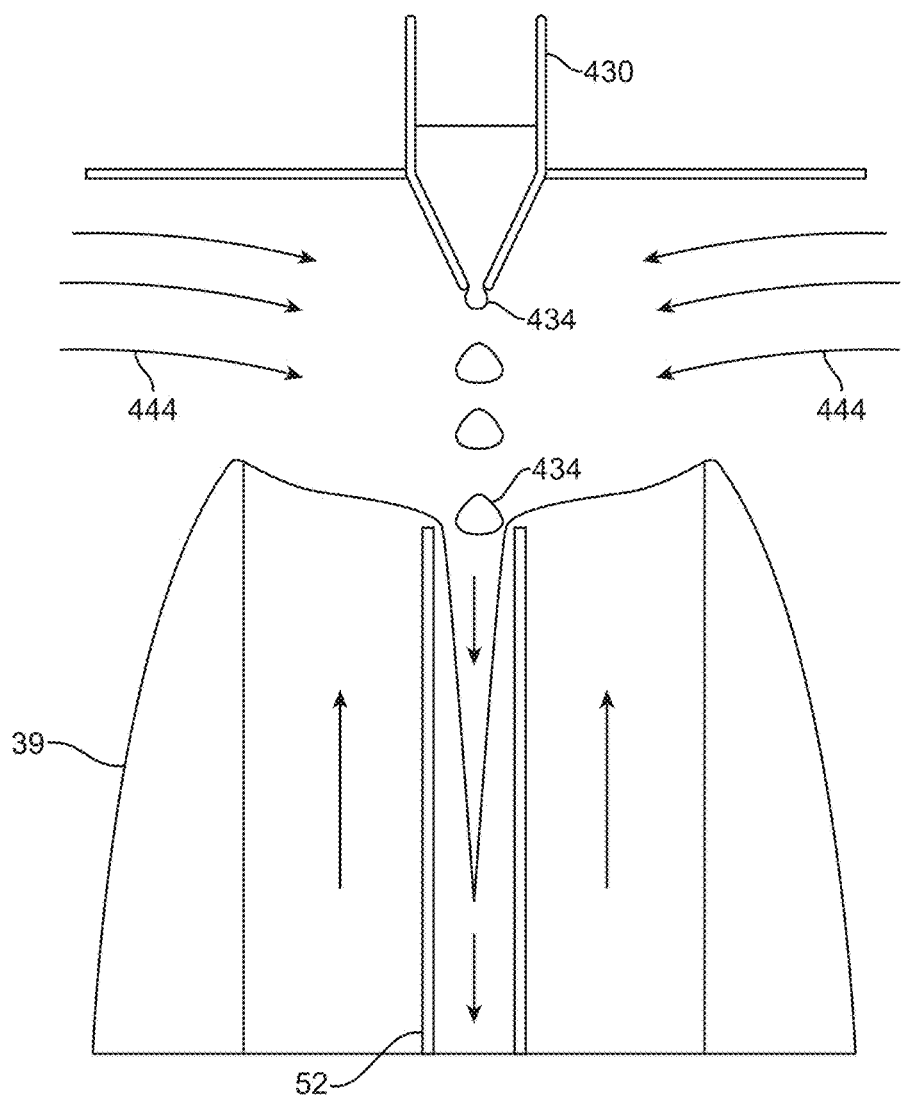
FIG. 21 is a schematic diagram of a droplet dispenser for supplying sample to the probe

It is possible to direct sample into the capture probe by means other than ejecting the sample from a sample material. There is shown in FIG. 21A a schematic diagram of a droplet dispenser 430 for supplying sample to the probe 39. The droplet dispenser can contain solvent and sample from any source, and can be oriented in any direction to direct droplets into or toward the probe by any suitable means. The droplets 434 can be sized by the flow rate and orifice diameter of the droplet dispenser 430 such that the diameter of the droplets 434 can be less than the diameter of the liquid exhaust conduit 52 and can be dispensed directly into the liquid exhaust conduit 52. Gas flow 444 into the exhaust conduit guides the sample droplets 442 into the liquid exhaust conduit 52.

A method for sampling a surface can include the step of directing sample into a capture probe. The directing step can include the step of providing a sample support for retaining a sample. A device such as a radiation energy source, an acoustic ablation source, or a droplet dispenser can be provided for directing sample into the probe, for example by a beam of radiation striking the sample such that sample is ejected into the probe. A probe is provided having an open end. The open end can be positioned a distance from the sample and the sample support to define a sample space. Liquid can be supplied to the open end of the probe at a first volumetric flow rate. The liquid can be removed from the open end of the probe at a second volumetric flow rate, the second volumetric flow rate exceeding the first volumetric flow rate. The radiation energy source can be operated to eject sample material from the sample. The ejected sample material and gas from the sample space can be removed with the liquid removed from the open end of the probe. The removed liquid containing sample and gas can be subjected to chemical analysis. The liquid removed from the open end can form a vortex. The method can further include the step of providing a gas guide between the open end of the probe and the sample for focusing the flow of gas into the liquid exhaust conduit. The method can further include the step of creating a voltage difference between the sample and the probe.

The method can further include the step of performing chemical analysis on liquid drawn into and passing through the exhaust conduit. The chemical analysis device can be at least one selected from the group consisting of high performance liquid chromatography and mass spectrometry. The analytical instrument for example can be any instrument utilized for analyzing analyte solutions. Exemplary analytical instruments include, but are not limited to, mass spectrometers, ionization sources, spectroscopy devices, separation methods, and combinations thereof. Exemplary ionization sources include, but are not limited to electrospray ionization (ESI), atmospheric pressure chemical ionization (APCI), electrospray chemical ionization (ESCi), atmospheric pressure photo-ionization (APPI) or inductively coupled plasma (ICP). Exemplary separation methods include, but are not limited to liquid chromatography, solid phase extraction, HPLC, capillary electrophoresis, or any other liquid phase sample cleanup or separation process. Exemplary mass spectrometers include, but are not limited to, sector time-of-flight, quadrupole mass filter three-dimensional quadrupole ion trap, linear quadrupole ion trap, Fourier transform ion cyclotron resonance orbitrap and toroidal ion trap.

Figure 20:
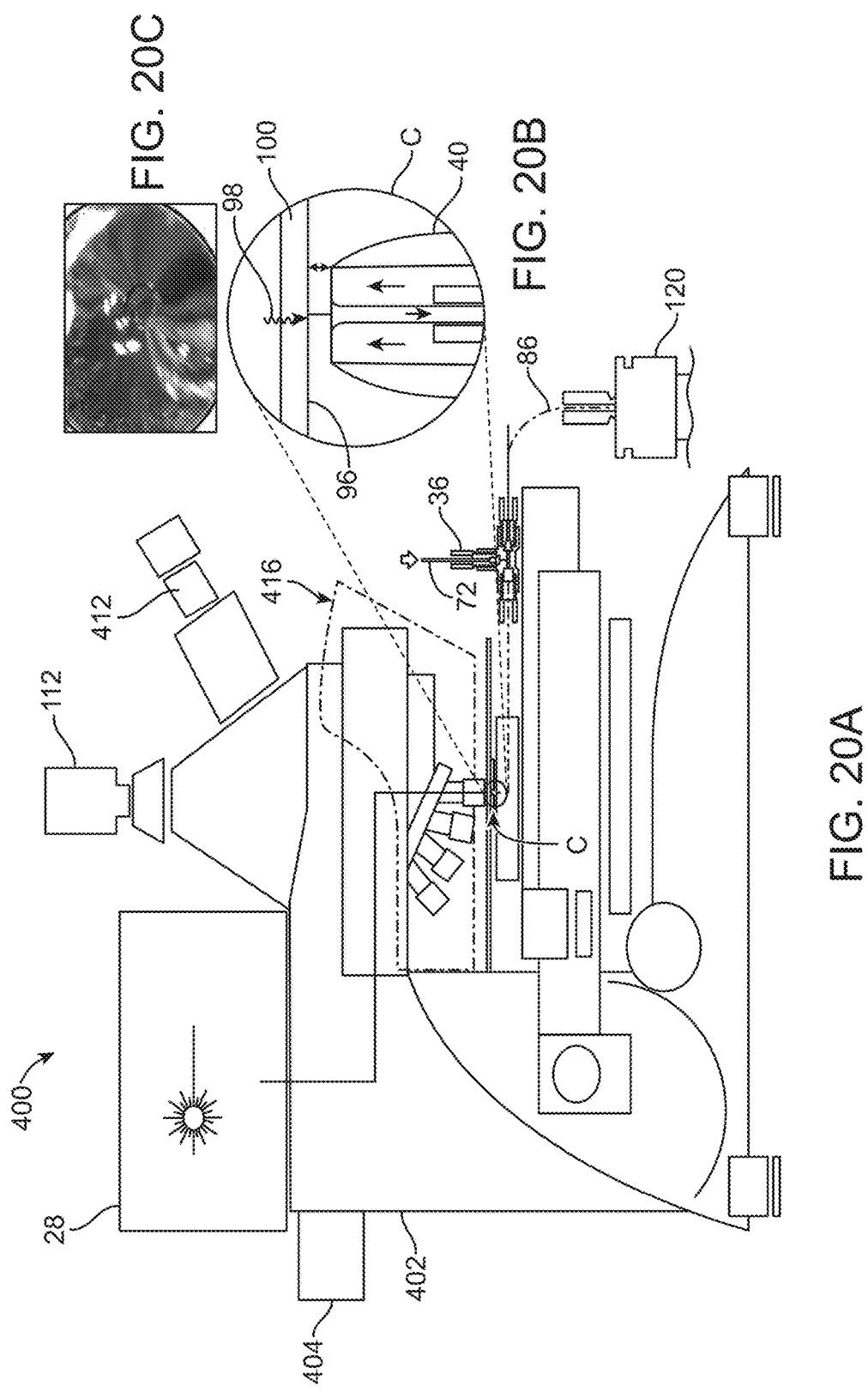
FIG. 20 is FIG. 20A a schematic diagram of a system for sampling a surface.

A processor 404 shown in FIG. 20 can be provided to control operation of the device, and particularly the flow rates of the liquid supply, liquid exhaust and vortex as desired. The processor can also control the operation of the sample-supplying device such as the laser 200. The processor can receive sensor signals and provide control signals to suitable valves and control circuitry to control operation of these devices and the system in general.

The system of the invention can also be operated in an overflow mode in which the first volumetric flow rate exceeds the second volumetric flow rate. Such a system is described in a copending United States patent application entitled "Open Port Sampling Interface" filed on even date herewith, the disclosure of which is hereby fully incorporated by reference.

Ranges: throughout this disclosure, various aspects of the invention can be presented in a range format. It should be understood that the description in the range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range for example, 1, 2, 2.7, 3, 4, 5, 5.3 and 6. This applies regardless of the breadth of the range.

This invention can be embodied in other forms without departing from the spirit or essential attributes thereof, and accordingly, reference should be had to the following claims to determine the scope of the invention.

We claim:

1. A system for sampling a sample material, comprising: a probe comprising an outer probe housing having an inner wall and an open end for communicating with a sample space; a liquid supply conduit within the housing and having an outlet positioned to deliver liquid to the open end of the housing; an exhaust conduit within the housing for removing liquid from the open end of the housing; the liquid supply conduit being connectable to a liquid supply for delivering liquid at a first volumetric flow rate to the open end of the housing; a liquid exhaust system in fluid connection with the liquid exhaust conduit for removing liquid from the liquid exhaust conduit at a second volumetric flow rate, the second volumetric flow rate exceeding the first volumetric flow rate, a gas flow containing sample flowing into and through the liquid exhaust conduit creating a gas/liquid interface in the liquid exhaust conduit; and, a device for directing sample into the open end of the probe communicating with the sample space.

2. The system of claim 1, wherein the device for directing sample into the probe is a laser producing a laser beam.

3. The system of claim 2, wherein the sample is provided on a support that is transparent to the wavelength and the laser is positioned to direct the laser beam through the support to the sample.

4. The system of claim 2, wherein the laser is positioned on the same side of the support as the sample.

5. The system of claim 1, wherein the second volumetric flow rate exceeds the first volumetric flow rate by at least 5%.

6. The system of claim 1, wherein the second volumetric flow rate exceeds the first volumetric flow rate by between 5-50%.

7. The system of claim 1 wherein the probe produces a vortex of liquid in the liquid exhaust conduit.

8. The system of claim 1, further comprising a gas guide between the open end of the probe and the sample for focusing the flow of gas into the liquid exhaust conduit.

9. The system of claim 1, further comprising a voltage source electrically connected to create a voltage difference between the sample surface and the probe.

10. The system of claim 1, wherein the device for directing sample into the probe comprises an acoustic desorption device.

11. The system of claim 1, wherein the device for directing sample into the probe comprises a droplet dispenser.

12. The system of claim 1, further comprising an analysis device in liquid communication with the liquid exhaust system.

13. A method for sampling a sample material, comprising the steps of: providing a probe having an open end communicating with a sample space; providing a device for directing sample into the open end of the probe; supplying liquid to the open end of the probe at a first volumetric flow rate; removing the liquid from the open end of the probe at a second volumetric flow rate, the second volumetric flow rate exceeding the first volumetric flow rate; operating the device to direct sample into the open end of the probe communicating with the sample space; removing the sample material and gas with the liquid removed from the open end of the probe through an exhaust conduit of the probe; and a gas flow containing sample flowing into and through the exhaust conduit creating a gas/liquid interface in the exhaust conduit.

14. The method of claim 13, wherein the device for directing sample into the probe is a radiation source for directing a radiation beam at sample material on a sample support.

15. The method of claim 14, wherein the radiation source is a laser.

16. The method of claim 15, wherein the sample is provided on a support that is transparent to the wavelength and the laser is positioned to direct the laser beam through the support to the sample.

17. The method of claim 15, wherein the laser beam emanates from the same side of the support as the sample.

18. The method of claim 13, further comprising the step of subjecting the removed liquid containing sample and gas to chemical analysis.

19. The method of claim 13, wherein the liquid removed from the open end forms a vortex in a liquid exhaust conduit.

20. The method of claim 13, wherein the device for directing sample into the probe is a droplet dispenser.

21. The method of claim 13, wherein the second volumetric flow rate exceeds the first volumetric flow rate by at least 5%.

22. The method of claim 13, wherein the second volumetric flow rate exceeds the first volumetric flow rate by between 5-50%.

23. The method of claim 13, further comprising the step of providing a gas guide between the open end of the probe and the sample for focusing the flow of gas into the liquid exhaust conduit.

24. The method of claim 13, further comprising the step of creating a voltage difference between the sample and the probe.

25. The method of claim 13, wherein the device for directing sample into the probe is an acoustic desorption energy source.

26. The method of claim 13, further comprising directing sample material and gas with the liquid removed from the probe to an analysis device.

27. A sampling probe system, comprising: an outer probe housing having an inner wall and an open end for communicating with a sample space; a liquid supply conduit within the housing and having an outlet positioned to deliver liquid to the open end of the housing; an exhaust conduit within the housing for removing liquid from the open end of the housing; the liquid supply conduit being connectable to a liquid supply for delivering liquid at a first volumetric flow rate to the open end of the housing; and, a liquid removal system in fluid connection with the liquid exhaust conduit for removing liquid from the liquid exhaust conduit at a second volumetric flow rate, the second volumetric flow rate exceeding the first volumetric flow rate, a gas flow containing sample flowing into and through the liquid exhaust conduit creating a gas/liquid interface in the liquid exhaust conduit.

28. The sampling probe system of claim 27, wherein liquid enters the liquid exhaust conduit as a vortex.

* * * * *